(12) United States Patent
Yamamoto et al.

(10) Patent No.: US 8,716,440 B2
(45) Date of Patent: May 6, 2014

(54) METHOD OF LIBERATING AND RECOVERING PEPTIDE

(75) Inventors: Yuta Yamamoto, Nagoya (JP); Kana Kawasaki, Kobe (JP); Hiroyuki Kabata, Kyoto (JP)

(73) Assignee: Sysmex Corporation, Hyogo (JP)

( * ) Notice: Subject to any disclaimer, the term of this patent is extended or adjusted under 35 U.S.C. 154(b) by 71 days.

(21) Appl. No.: 13/458,014

(22) Filed: Apr. 27, 2012

(65) Prior Publication Data

US 2012/0277407 A1 Nov. 1, 2012

(30) Foreign Application Priority Data

Apr. 28, 2011 (JP) ................................ 2011-101588

(51) Int. Cl.
*C07K 1/14* (2006.01)
*G01N 1/44* (2006.01)

(52) U.S. Cl.
USPC ............................................ 530/344; 436/86

(58) Field of Classification Search
None
See application file for complete search history.

(56) References Cited

U.S. PATENT DOCUMENTS 544,912 A * 8/1895 Finsen ......................... 530/364

OTHER PUBLICATIONS

Mark S. Lowenthal et al., "Analysis of Albumin-Associated Peptides and Proteins from Ovarian Cancer Patients", Clinical Chemistry: Oak Ridge Conference, 2005, pp. 1933-1945, vol. 51, No. 10.
Ming Zhou et al., "An investigation in the human serum interactome", Electrophoresis, 2004, pp. 1289-1298, vol. 25.

* cited by examiner

*Primary Examiner* — Jeffrey E Russel
(74) *Attorney, Agent, or Firm* — Sughrue Mion, PLLC

(57) ABSTRACT

A novel method capable of liberating a peptide from a complex of peptide and albumin and the associated method of recovering the peptide are provided. When a liquid sample containing a complex of peptide and albumin undergoes heat treatment, a self-aggregate of albumin formed in the liquid sample. The peptide is simultaneously liberated from the complex and recovered by removing the self-aggregate from the liquid sample.

10 Claims, 3 Drawing Sheets

METHOD OF LIBERATING AND RECOVERING PEPTIDE

FIELD OF THE INVENTION

The present invention relates to a method of liberating a peptide of interest from its complex with albumin. The present invention accompanies a method of recovering the peptide based on the method of the peptide liberation.

BACKGROUND

There is a wide variety of peptides in blood. These peptides include peptides that clearly indicate the differences in concentrations in blood between healthy and pathologic conditions. Such characteristic peptides are regarded to be biomarkers for diseases and to be beneficial to clinical test. For example, it is known that the concentration of ghrelin in plasma decreases in the case of patients suffering a gastric cancer associated with serious heart failure and severe cachexia. Because the concentration of brain natriuretic peptide (BNP) in blood is important as a clinical index of heart failure, the peptide is used as a test marker.

There is a large amount of protein referred to as "albumin" in blood. The albumin protein is known to inhibit detection of peptides in blood. In order to remove albumin from a sample of blood, a method has been conventionally performed in which the blood sample is loaded onto a column adsorbing specifically albumin. Albumin in the blood sample remains on the column, while a liberating form of peptides pass and were collected. (Lowenthal M S et al. "Anaysis of albumin-associated peptides and proteins from ovarian cancer patients", Clin. Chem., vol. 51, 1933-1945 (2005)) and Zhou M et al., "An investigation into the human serum interactome", Electrophoresis., vol. 25, 1289-1298 (2004)).

However, the recent reports have showed that most peptides in blood bind to albumin to form a complex. For example, Lowenthal et al. have disclosed 98% of peptides in serum are bound to and complexed with albumin. That is, by the column method of adsorbing albumin and passing peptides, peptides undesirably remain with the column-adsorbed albumin and were abolished upon disposal of the column. Consequently, only a very small amount of the peptides are obtained.

SUMMARY OF THE INVENTION

The scope of the present invention is defined solely by the appended claims, and is not affected to any degree by the statements within this summary.

An objective of the present invention is to provide a novel method capable of liberating a peptide from a complex of peptide and albumin. Another objective of the present invention is to provide a method of recovering a peptide using the liberation method.

The present inventors have found the following surprising fact. When a liquid sample containing a complex of peptide and albumin is heat-treated, albumin forms an aggregate autonomously (hereinafter referred to as "self-aggregate") and precipitates simultaneously, and thus the peptide is liberated from the precipitating albumin. Accordingly, they have completed the present invention.

A first aspect of the present invention is a method of liberating a peptide, comprising:
liberating the peptide from its complex with albumin in a liquid sample by heat-treatment of the liquid sample and the subsequent formation of a self-aggregate of albumin.

A second aspect of the present invention is a method of recovering a peptide, comprising:
liberating the peptide from its complex with albumin in a liquid sample by heat-treatment of the liquid sample and the subsequent formation of a self-aggregate of albumin; and
recovering the liberated peptide by removing the self-aggregate from the heat-treated liquid sample.

According to the present invention, a peptide is able to be liberated from a complex of the peptide and albumin. In addition, according to the present invention, the peptide liberated from the complex is able to be efficiently recovered.

DETAILED DESCRIPTION OF THE PREFERRED EMBODIMENTS

Figure 1:
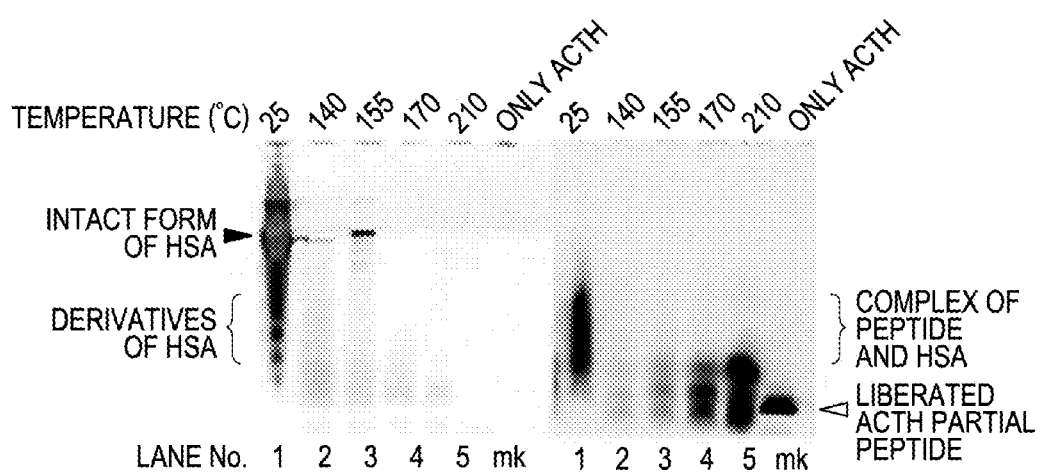
FIG. 1 is a photographed gel showing respectively human serum albumin (hereafter, HSA) and a NH3-terminal portion of the ACTH peptide (hereafter, ACTH partial peptide) that originally existed as a complex in a liquid sample. The liquid sample was heat-treated for 120 minutes at various temperatures indicated above the lanes. Then the resultant supernatant was electrophoresed through the gel. HSA in the supernatant was visualized as bands or smears by silver staining the gel (left panel), while the ACTH partial peptide was done by fluorescent scanning the same gel (right). A standard electrophoretic migration marker is denoted as mk.

The preferred embodiments of the present invention will be described hereinafter with reference to the drawings.

The method of the present invention for liberating a peptide of interest (hereinafter simply referred to as "liberation method") includes heat-treating a liquid sample that contains a complex of the peptide and the albumin protein, forming a self-aggregate of the protein, and then liberating the peptide.

The liberation method and the method for recovering a peptide of the present invention are able to be used as pre-treatment for detecting a peptide contained in a liquid sample. This is because the method of the present invention is able to separate the peptide from its complex with albumin, which is an inhibitor of peptide detection, and to give a preferred form of the peptide for measuring peptides.

The term "albumin" used herein has the same meaning as the term generally known in the field of biology and is a generic term for a group of soluble proteins contained in animal and plant cells or body fluids.

In the embodiment of the present invention, the albumin is not particularly limited as long as it is an undenatured albumin. Examples of the albumin derived from animals include serum albumin contained in serum, ovalbumin contained in albumen, and lactalbumin contained in milk. Examples of the albumin derived from vegetables include leucosin contained in wheats and barleys, legumelin contained in seeds such as peas and soybeans, and ricin contained in castor seeds.

In the embodiment of the present invention, the liquid sample is not particularly limited as long as it contains the complex of peptide and albumin. In the art (Lowenthal M S et al.), it is known that undenatured albumin proteins tend to bind to peptides to form complexes. Therefore, when a peptide or peptides and undenatured albumin coexist in liquid, complex or complexes between them simultaneously forms in the liquid. The liquid is thus a subject of the present invention, serving as the liquid sample.

In a preferred embodiment of the present invention, the liquid sample is a biological sample. Examples of the biological sample include blood and body fluid collected from individuals. Other examples thereof include plasma and serum of blood.

In the embodiment of the present invention, the amount of the liquid sample is not particularly limited. In case that the liquid sample is in a small amount, the water content of the sample should be kept at a level where the sample is never dried out after the heat-treatment mentioned below.

In the embodiment of the present invention, the peptide is not particularly limited, and it may be a naturally occurring peptide or a synthetic peptide. The peptide has preferably a length of 10 to 100 amino acids, more preferably a length of 10 to 60 amino acids, still more preferably a length of 10 to 40 amino acids.

In the embodiment of the present invention, the isoelectric point of the peptide is not particularly limited. The peptide may be any of a basic peptide, an acidic peptide, and a neutral peptide.

In the embodiment of the present invention, when the liquid sample is a biological sample, the peptide is a peptide present in the biological sample. Some of the peptide can be contained in blood, plasma, serum, and other body fluids, which are derived from individuals. In the embodiment of the present invention, the peptide is preferably a biomarker present in the blood.

Examples of the peptide as the biomarker include Ghrelin, brain natriuretic peptide (BNP), adrenocorticotropic hormone (ACTH), atrial natriuretic polypeptide (ANP), bradykinin, α-endorphin, C peptide, C3f fragment, ITIH4 fragment, and Aβ peptide. However, they are not limited thereto.

In the present invention, the peptide to be liberated can be one that consists of an unidentified sequence of amino acids, for example.

In the embodiment of the present invention, the time and temperature of the heat-treatment for the liquid sample can be adjusted to give the following results. The peptide in the liquid sample is moderately preserved although undergoes degradation by heat to some extent. Here, a "moderately preserved" peptide is defined as a peptide that is partially cleaved at limited position(s) of its amino acid sequence and substantially same as before the heat-treatment. An opposite "thoroughly degraded" peptide is defined as a peptide are randomly fragmented to an undetectable level like to single amino acids. That is, in the liberation method of the present invention, most of the peptides liberated from their complexes with albumin remain intact and show a higher quality than "moderately preserved" peptides. In the embodiment of the present invention, some of the "moderately preserved" peptides lack a few amino acids near the termini of the whole peptide sequences. However, the peptide of interest in the liquid sample is never "thoroughly degraded", as long as the heat-treatment of the liberation method of the present invention is appropriately performed.

In the embodiment of the present invention, more specifically, the heat-treatment includes heating at 140 to 260° C. for 5 minutes to 19 hours. In a preferred embodiment of the present invention, when the heating temperature is 140° C. or more and less than 155° C., the heating time is at least 90 minutes or more, particularly 120 minutes or more. When the heating temperature is 155° C. or more and less than 170° C., the heating time is preferably at least 20 minutes or more. When the heating temperature is 170° C. or more, the heating time is preferably at least 5 minutes or more.

In the embodiment of the present invention, a container in which a liquid sample is reserved of heat-treatment is not particularly limited, in so far as being a container made of a material resistant to the heat-treatment. Examples thereof include containers made of materials such as heat-resistant glass and resin. In the case that the amount of the liquid sample is small, a container that is less adsorptive for the peptide is preferable to contain the sample. These containers are generally available.

In the embodiment of the present invention, the method of heat treatment is not particularly limited as long as it is a method capable of heating the liquid sample at the temperatures mentioned above. The method may be selected from known methods in the art. Examples of the method include a method of external heating by conduction and a method of internal heating by microwave.

In the embodiment of the present invention, the apparatus of heat treatment is not particularly limited as long as it is an apparatus which heats the liquid sample at controlled temperatures. A hydrothermal reaction vessel and a microwave irradiation device are used, for example.

The liberation method of the present invention makes it possible to convert albumin in the liquid sample from a form of complex with peptide to a form of self-aggregate by the heat-treatment. It is reasonable that almost all the molecules of the self-aggregate of albumin lose the ability to bind peptides due to perturbation in albumin's structure upon heat treatment. In the liberation method of the present invention, the peptide is consequently liberated upon the formation of the self-aggregate of albumin.

The self-aggregate of albumin is insoluble in a solvent contained in the liquid sample and precipitates in the heat-treated liquid sample. That is, the heat-treated liquid sample is divided into two fractions: precipitate containing the self-aggregate of albumin and supernatant containing peptides.

In the embodiment of the present invention, the peptide liberated from albumin is able to be identified as the expected free form in the supernatant fraction using any known method in the art. Examples of the method include electrophoresis and mass spectrometry.

The method of recovering a peptide of the present invention (hereinafter simply referred to as "recovery method") includes the following steps:
(1) heat-treating a liquid sample containing a complex of peptide and albumin to form a self-aggregate of albumin and liberating the peptide from albumin (hereinafter referred to as "liberation step"); and
(2) removing the self-aggregate from the heat-treated liquid sample to recover the liberated peptide (hereinafter referred to as "recovery step").

In the recovery method of the present invention, contents of the liberation step are eventually same as in the description of the liberation method of the present invention.

In the recovery step, the method of removing the self-aggregate of albumin from the heat-treated liquid sample is not particularly limited. For example, the self-aggregate of albumin may be directly removed using a spatula. Alternatively, the self-aggregate may be removed using a commercially available separator or filter paper. Thus, in the recovery method of the present invention, peptides can be recovered by removing the self-aggregate of albumin from the heat-treated liquid sample and obtaining the supernatant fraction containing the liberated peptides.

As described above, the self-aggregate of albumin is not bound to the peptide. However, the self-aggregate of albumin is hydrophilic and adsorbs a part of the supernatant containing peptides, as in the case of a water absorbable sponge.

Therefore, the recovery method of the present invention may further include a step of obtaining the residual supernatant containing peptides from the removed self-aggregate of albumin. In the step of obtaining the residual supernatant containing peptides from the self-aggregate of albumin, for example, the self-aggregate is transferred into a tube with ultrafilter and centrifuged to squeeze the supernatant out. Alternatively, the supernatant may be obtained by stirring the self-aggregate with a homogenizer. The step of obtaining the residual supernatant from the self-aggregate needs no heat treatment.

Hereinafter, the present invention will be described more in detail, however, the present invention is not limited thereto.

EXAMPLES

Example 1

(1) Preparation of Liquid Sample Containing Complex of Peptide and Albumin

ACTH partial peptide consisting of 1st to 24th amino acids of ACTH (PEPTIDE INSTITUTE, INC.) and TMR-ACTH partial peptide in which the above peptide was labeled with tetramethyl rhodamine (TMR) (a red fluorescent dye) (Biologica Co, Ltd.) were used as peptides. The ACTH is a basic peptide. The used albumin was human serum albumin (HSA, Sigma-Aldrich Japan Inc.). The peptide and HSA were dissolved in ultrapure water to prepare a liquid sample containing a complex of peptide and albumin (concentration of ACTH partial peptide: 34 µM, concentration of TMR-ACTH partial peptide: 6 µM, concentration of HSA: 600 µM). The equilibrium dissociation constant (Kd) among the HSA, ACTH partial peptide, and TMR-ACTH partial peptide was measured by a fluorescence titration method and the Kd value was 6 µM. That is, in the solution prepared in the above manner, 98.9% of the ACTH partial peptide and TMR-ACTH partial peptide formed a complex with the HSA.

(2) Heat-Treatment of Liquid Sample

The liquid sample (3 mL) was transferred to a 10-mL volume glass test tube. The tube was sealed with a pressure resistant sealing holder for Teflon test tubes (Milestone General K.K.) and placed in a microwave applicator (Multi-SYNTH type, Milestone General K.K.). Then, Heat-treatment was performed at 140, 155, 170, and 210° C. for 120 minutes. The time until the temperature (temperature regulation at 25° C.) in the laboratory where this example was performed reached the four temperatures, namely, the rate of temperature increase was 35° C./m in each case. Cooling after heating was performed by blowing compressed air to the pressure resistant sealing holder from an air compressor (YC-3 R type, Yaezakiku-atu. Co., Ltd.) connected to the microwave applicator. The cooling rate was 20° C./min. As a control, the liquid sample (3 mL) was similarly sealed and kept warm at 25° C. for 120 minutes.

In addition to the method of heating by microwave irradiation, a method comprising pouring the liquid sample (3 mL) in a sealed type dissolving crucible (MR-28 type, OM LAB-TECH CO., LTD.), placing the sealed crucible in an oven (FC-410 type, Advantec Toyo Kaisha, Ltd.), and heating by heat conduction from the oven was also performed. Then, the almost same result as that in the case of microwave irradiation was obtained.

Precipitates were observed in all the liquid samples heat-treated at each of the temperatures. On the other hand, no precipitate was observed in the liquid sample kept warm at 25° C.

(3) Detection of Peptide and Albumin

The supernatant fractions of the heat-treated liquid samples were used as samples and SDS-PAGE was performed on the samples. The above samples were heat-treated at 70° C. for 10 minutes using NuPAGE LDS Sample Buffer and NuPAGE Sample Reduction Agent (both products are manufactured by Life Technologies Corporation). Then, electrophoresis was performed at 200 V (constant voltage) for 30 minutes using NuPAGE 4-12% Bis-Tris Gel and NuPAGE MES SDS Running Buffer (both products are manufactured by Life Technologies Corporation). The used electrophoresis tank was X-Cell Sure Lock Minicell (Life Technologies Corporation.) and the used electric power unit was Power Station 1000XP (ATTO Corporation). As for the gel after electrophoresis, the TMR-ACTH partial peptide was detected using a fluorescence imager (Pharos FX Molecular Imager type, Bio-Rad Laboratories, Inc.) and the HSA was detected by silver staining. In the silver staining, a silver stain kit (EzStain Silver, ATTO Corporation) was used. Respective staining steps are as follows: Immobilizing: shaking with 100 mL of a fixative (40 mL of ultrapure water, 50 mL of methanol, 10 mL of acetic acid, and 1 mL-kit bottle S-1) for 10 minutes; Washing: shaking with 100 mL of ultrapure water three times for 10 minutes; Staining: shaking with a stain solution (100 mL of ultrapure water and a 1 mL-kit bottle S-2) for 10 minutes; Washing: shaking with 100 mL of ultrapure water for 30 seconds shaking with 100 mL of a coloring liquid (200 mL of ultrapure water, a 1 mL-kit bottle S-3, a 1 mL-kit bottle S-4) for 30 seconds; Coloring: shaking with 100 mL of a coloring liquid for 5 to 10 minutes, Terminating; shaking with 100 mL of a stop solution (100 mL of ultrapure water, 1 mL of acetic acid) for 10 minutes; Washing: shaking with 100 mL of ultrapure water twice for 5 minutes. The used shaker was In vitro shaker Wave-SI (TAITEC CORPORATION). The results are shown in FIG. 1. In FIG. 1, the mark "mk" indicates a lane in which only the TMR-ACTH partial peptide was electrophoresed as a size marker.

In the left panel of FIG. 1, an intact form of the HSA and a band of derivatives having a molecular weight lower than that of the HSA were observed in the liquid sample kept warm at 25° C. That is, it is found that the dissolved albumin is present in the liquid sample kept warm at 25° C. In the right panel of FIG. 1, as for the liquid sample kept warm at 25° C., a fluorescent signal was detected in the almost same position as that of the derivatives of the HSA. As for the TMR-ACTH partial peptide, no signals appear in the position as is clear from the lane of "mk". Therefore, it is found that, in the liquid sample kept warm at 25° C., the TMR-ACTH partial peptide is present by forming a complex with the HSA.

On the other hand, in the left panel of FIG. 1, the band of HSA was hardly observed in the liquid sample heat-treated at each of the temperatures. In the right panel of FIG. 1, as for the heat-treated liquid sample, the band was observed in the same position as that of the lane of "mk" in which only the TMR-ACTH partial peptide was electrophoresed. These results suggest that the HSA in the heat-treated liquid sample was self-associated and precipitated, and thus the ACTH partial peptide was liberated from the HSA at that time.

Example 2

(1) Preparation of Liquid Sample

A liquid sample containing a complex of peptide and albumin (concentration of ACTH partial peptide: 34 (M, concentration of TMR-ACTH partial peptide: 6 (M, concentration of BSA: 600 (M) was prepared in the same manner as described in Example 1 except that bovine serum albumin (BSA, Sigma-Aldrich Japan Inc.) was used as albumin.

(2) Heat-Treatment of Liquid Sample

The liquid sample (3 mL) was heat-treated in the same manner as described in Example 1. The heating temperature and the time are as follows: (i) Heat-treatment at 130, 140, 155, and 170° C. for 5 minutes; (ii) Heat-treatment at 50, 105, 120, 140, and 150° C. for 60 minutes; and (iii) Heat-treatment at 25, 130, and 140° C. for 1110 minutes.

(3) Detection of Peptide and Albumin

Figure 2:
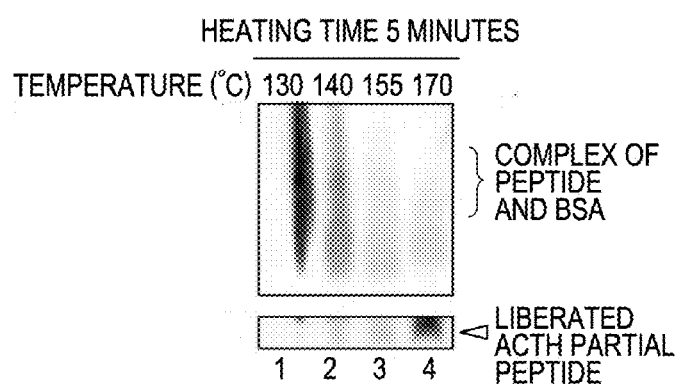
FIG. 2 is a photographed gel showing respectively bovine serum albumin (hereafter, BSA) and the ACTH partial peptide that originally existed as a complex in a liquid sample. The liquid sample was heat-treated for 5 minutes specified at various temperatures (indicated above the lanes). Then the resultant supernatant was electrophoresed through the gel. HSA in the supernatant was visualized as bands or smears by silver staining the gel (upper panel), while the ACTH partial peptide was done by fluorescent scanning the same gel (lower)
Figure 3:
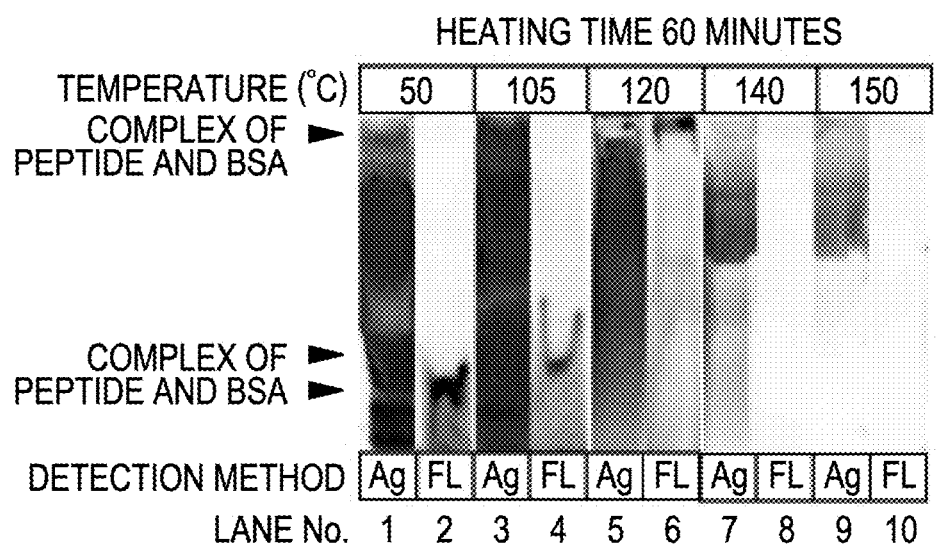
FIG. 3 is an arranged set of lanes of a photographed gel showing respectively BSA and the ACTH partial peptide that originally existed as a complex in a liquid sample. The liquid sample was heat-treated for 60 minutes at various temperatures indicated above the lanes. Then the resultant supernatant was electrophoresed through the gel. HSA in the supernatant was visualized as bands or smears by silver staining the gel (lanes odd-numbered, denoted as Ag), while the ACTH partial peptide was done by fluorescent scanning the same gel (lanes even-numbered, denoted as FL)
Figure 4:
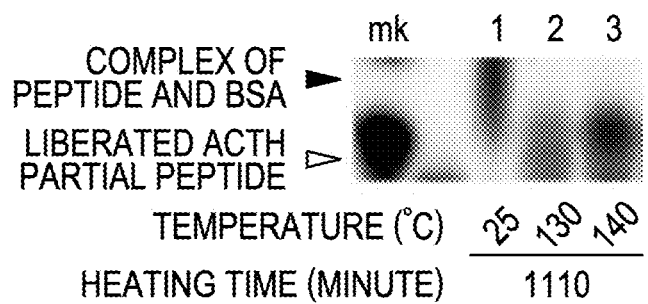
FIG. 4 is a photographed gel showing exclusively the ACTH partial peptide that originally existed as a complex with BSA (lane 1) in a liquid sample. The liquid sample was heat-treated for 1,110 minutes at lower temperatures indicated below the lanes, and the resultant supernatant was electrophoresed through the gel. Only a trace amount of the ACTH partial peptide was liberated in the supernatant (lanes 2 and 3)

The albumin and peptide in the heat-treated liquid samples were detected in the same manner as described in Example 1. The results are shown in FIGS. 2 to 4. In FIG. 3, the mark "Ag" means staining with silver and the mark "FL" means fluorescent imaging. FIGS. 2 and 4 show only the results of fluorescent imaging.

In the upper panel on FIG. 2, when the time of heat-treatment was 5 minutes, the TMR-ACTH partial peptide forming a complex with the BSA was observed in the lanes (No. 1 to 3) in which the heating temperatures were 130, 140, and 155° C. On the other hand, the band of the liberated TMR-ACTH partial peptide was clearly observed in the lane (No. 4) in which the heating temperature was 170° C. From these results, it is found that when the time of heat-treatment is short, the heat-treatment needs to be performed at relatively high temperatures.

In FIG. 3, when the heat-treatment time was 60 minutes, the BSA was stained with silver and the TMR-ACTH partial peptide forming a complex with the BSA was observed in lanes (No. 1 to 6) in which the heating temperatures were 50, 105, and 120° C. On the other hand, bands of BSA were considerably decreased and the complex of BSA and TMR-ACTH partial peptide was not observed in lanes (No. 7 to 10) in which the heating temperatures were 140 and 150° C. As a result, it is suggested that the heating temperature needs to be 140° C. or more to remove the albumin.

In FIG. 4, when the time of heat-treatment was 1110 minutes (18.5 hours), the complex of BSA and TMR-ACTH partial peptide was still observed in the lane (No. 1) in which the heating temperature was 25° C. In the lane (No. 2) in which the heating temperature was 130° C., the band of the liberated TMR-ACTH partial peptide was not sufficiently detected. On the other hand, in the lane (No. 3) at a heating temperature of 140° C., a band of the liberated TMR-ACTH partial peptide was clearly detected. These results suggest that the heating temperature needs to be at least 140° C. or higher to liberate the peptide from the complex of peptide and albumin.

Example 3

(1) Preparation of Liquid Sample

FITC-SA21 (Biologica Co, Ltd.) in which SA21 consisting of 18 amino acids was labeled with fluorescein isothiocyanate (FITC) (a green fluorescent dye) was used as a peptide. The SA21 is an acidic peptide. The used albumin was BSA (Sigma-Aldrich Japan Inc.). The peptide and BSA were dissolved in ultrapure water to prepare a liquid sample containing a complex of peptide and albumin (concentration of FITC-SA21: 43 (M, concentration of BSA: 100 (M). The Kd value between the BSA and FITC-SA21 was measured by the fluorescence titration method and the value was 1 (M or less. This showed that the affinity of binding between the BSA and FITC-SA21 was 6 times stronger than the affinity of binding between the HSA and ACTH partial peptide. That is, in the solution prepared in the above manner, 98.3% of FITC-SA21 formed a complex with the HSA.

(2) Heat-Treatment of Liquid Sample

The liquid sample (1 mL) was heat-treated in the same manner as described in Example 1. The heating temperature and the time are as follows: (i) Heat-treatment at 140° C. for 120 minutes; (ii) Heat-treatment at 170° C. for 5, 30, and 120 minutes; and (iii) Heat-treatment at 200° C. for 5 minutes.

(3) Detection of Peptide and Albumin

Figure 5:
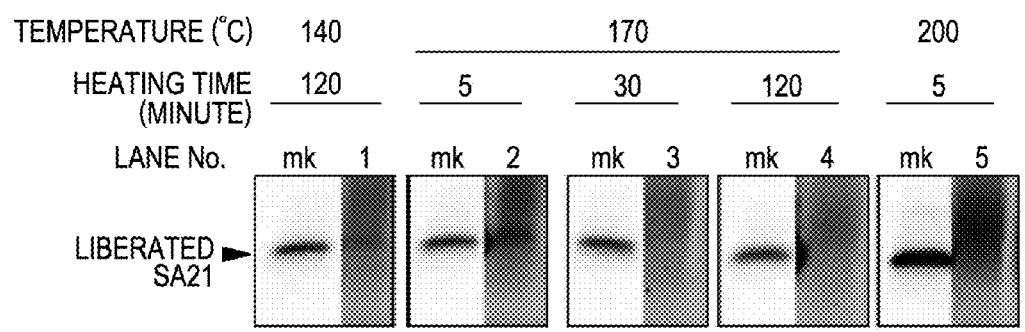
FIG. 5 is an arranged set of lanes of a photographed gel showing exclusively an acidic peptide SA21 that originally existed as a complex with BSA in a liquid sample. The liquid sample was heat-treated, and the resultant supernatant was electrophoresed through the gel.

The albumin and peptide in the heat-treated liquid samples were detected in the same manner as described in Example 1. The results are shown in FIG. 5. In FIG. 5, the mark "mk" indicates a lane in which only the FITC-SA21 was electrophoresed as a size marker.

FIG. 5 shows that the acidic peptide can be liberated from the albumin by heat-treating the liquid sample. Therefore, it is found that the method of liberating a peptide of the present invention is not influenced by the isoelectric point of the peptide.

Example 4

(1) Preparation of Liquid Sample

A liquid sample containing a complex of peptide and albumin (concentration of ACTH partial peptide: 91 (M, concentration of TMR-ACTH partial peptide: 9 (M, concentration of BSA: 100 (M) was prepared in the same manner as described in Example 1 except that bovine serum albumin (BSA, Sigma-Aldrich Japan Inc.) was used as albumin.

(2) Heat-Treatment of Liquid Sample

The liquid sample (1 mL) was heat-treated in the same manner as described in Example 1. The heating temperature and the time are as follows: (i) Heat-treatment at 170° C. for 30 minutes; and (ii) Heat-treatment at 200° C. for 5 minutes.

(3) Recovery of Supernatant Fraction from Self-Aggregate of Albumin

The self-aggregate of albumin produced by the heat-treatment of the liquid sample was subjected to centrifugal filtration using an ultrafiltration tube (Amicon Ultra, molecular weight cutoff, 10,000, Nihon Millipore K.K) or stirred with a micro homogenizer to recover a supernatant fraction of the liquid sample contained in the self-association. Centrifugal filtration and stirring were performed twice, respectively.

(4) Detection of Peptide and Albumin

Figure 6:
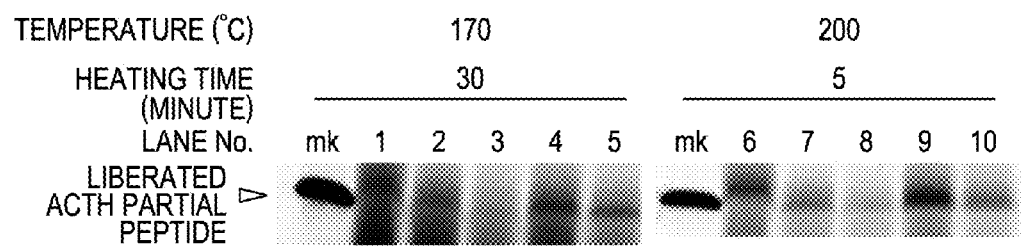
FIG. 6 is a photographed gel showing exclusively the ACTH partial peptide that originally existed as a complex with BSA in a liquid sample. The liquid sample was heat-treated. After the generated self-aggregates of BSA was treated by a physical method, the obtained supernatant was electrophoresed through the gel.

The albumin and peptide in the heat-treated liquid samples and the supernatant fraction recovered from the self-aggregate were detected in the same manner as described in Example 1. The results are shown in FIG. 6. In FIG. 6, the mark "mk" indicates a lane in which only the TMR-ACTH partial peptide was electrophoresed as a size marker. The electrophoresed samples in Lane No. 1 to 10 are shown in Table 1 below.

TABLE 1

| Lane No. | The electrophoresed sample |
| --- | --- |
| 1 and 6 | the supernatant fraction of the heat-treated liquid samples |
| 2 and 7 | the supernatant fraction recovered from the self-aggregate of albumin by the first Centrifugal filtration |
| 3 and 8 | the supernatant fraction recovered from the self-aggregate of albumin by the second Centrifugal filtration |
| 4 and 9 | the supernatant fraction recovered from the self-aggregate of albumin by the first stirring |
| 5 and 10 | the supernatant fraction recovered from the self-aggregate of albumin by the second stirring |

From FIG. 6, it is found that ACTH partial peptide could be liberated from a complex of ACTH partial peptide and BSA by the liberation method of the present invention. From Lane Nos. 2 to 10 of FIG. 6, it is found that the ACTH partial peptide is contained in the supernatant fraction recovered from the self-aggregate of BSA. Therefore, in the present invention, the supernatant fraction can be further recovered from the self-aggregate of albumin.

What is claimed is:

1. A method of liberating a peptide, comprising:
    liberating the peptide from its complex with albumin in a liquid sample by heat-treatment of the liquid sample and the subsequent formation of a self-aggregate of albumin, wherein the heat-treatment comprises heating at 140 to 260° C. for 5 minutes to 19 hours.

2. The method according to claim 1, wherein the heat-treatment is performed under conditions where the peptide in the liquid sample is moderately preserved after heating.

3. The method according to claim 1, wherein the liquid sample is a biological sample and the peptide is a peptide present in the biological sample.

4. The method according to claim 3, wherein the biological sample is blood, plasma, serum, or body fluid.

5. The method according to claim 1, wherein the peptide is a biomarker present in blood.

6. A method of recovering a peptide, comprising:
    liberating the peptide from its complex with albumin in a liquid sample by heat-treatment of the liquid sample and the subsequent formation of a self-aggregate of albumin; and
    recovering the liberated peptide by removing the self-aggregate from the heat-treated liquid sample, wherein the heat-treatment comprises heating at 140 to 260° C. for 5 minutes to 19 hours.

7. The method according to claim 6, wherein the heat-treatment is performed under conditions where the peptide in the liquid sample is moderately preserved after heating.

8. The method according to claim 6, wherein the liquid sample is a biological sample and the peptide is a peptide present in the biological sample.

9. The method according to claim 8, wherein the biological sample is blood, plasma, serum, or body fluid.

10. The method according to claim 6, wherein the peptide is a biomarker present in blood.

* * * * *